United States Patent [19]
Valenzuela et al.

[11] Patent Number: 5,965,140
[45] Date of Patent: *Oct. 12, 1999

[54] HYBRID PARTICLE IMMUNOGENS

[75] Inventors: Pablo D. T. Valenzuela; George Kuo, both of San Francisco; Philip J. Barr, Orinda, all of Calif.

[73] Assignee: Chiron Corporation, Emeryville, Calif.

[*] Notice: This patent is subject to a terminal disclaimer.

[21] Appl. No.: 09/132,079

[22] Filed: Aug. 10, 1998

Related U.S. Application Data

[63] Continuation of application No. 08/352,989, Dec. 9, 1994, Pat. No. 5,792,463, which is a continuation of application No. 08/126,115, Sep. 23, 1993, abandoned, which is a continuation of application No. 07/966,291, Oct. 26, 1992, abandoned, which is a continuation of application No. 07/128,639, Dec. 4, 1987, abandoned, which is a division of application No. 06/777,976, Sep. 19, 1985, Pat. No. 4,722,840, which is a continuation-in-part of application No. 06/650,323, Sep. 12, 1984, abandoned.

[51] Int. Cl.$^6$ .................. A61K 39/295; C12N 15/33; C07H 21/04
[52] U.S. Cl. ................... 424/202.1; 424/192.1; 424/227.1; 435/69.3; 435/69.9; 536/23.72
[58] Field of Search ............. 424/202.1, 192.1, 424/227.1; 435/69.3, 69.9; 536/23.72

[56] References Cited

U.S. PATENT DOCUMENTS 4,710,463  12/1987  Murray et al. .................. 435/69.3

FOREIGN PATENT DOCUMENTS 0072318  8/1982  European Pat. Off. .
0174759  8/1985  European Pat. Off. .

OTHER PUBLICATIONS

Ballou et al., "Immunogenicity of Synthetic Peptides From Circumsporozoite Protein of *Plasmodium Falciparum*," *Science* 228:996 (1985).
Bouges–Bocquet et al., *Chemical Abstracts* 101:185169g(1984).
Dame et al., "Structure of the Gene Encoding the Immunodominant Surface Antigen on Sporozoite of the Human Malaria Parasite *Plasmodium Falciparum*," *Science* 225: p. 593 (1984).
Edman et al., "Synthesis of Hepatitis B Surface and Core Antigens in *E. Coli*", *Nature* 291:503–506 (1981).
Enea et al., "DNA Cloning of *Plasmodium Falciparum* Circumsporozoite Gene: Amino Acid Sequence of Repetitive Epitope," *Science* 225:628 (1984).
Sharma and Godson, "Expression of the Major Surface Antigen of *Plasmodium Knowlesi* Sporozoites in Yeast," *Science* 228:879 (1985).
Valenzuela, P., et al., "The Nucleotide Sequence of the Hepatitis B Viral Genome and the Identification of the Major Viral Genes," *Animal Virus Genetics* pp. 57–70 (1980).
Valenzuela, P., et al., "Synthesis and Assembly of Hepatitis B Virus Surface Antigen Particles in Yeast," *Nature* 298:347–350 (1982).
Valenzuela, P., et al., "Antigen Engineering in Yeast: Synthesis and Assembly of Hybrid Hepatitis B Surface Antigen–Herpes Simplex 1 gD Particles," *Bio/Technology* 3:323–326 (1985).
Valenzuela, P., et al., "Nucleotide Sequence of the Gene Coding for the Major Protein of Hepatitis B Virus Surface Antigen," *Nature* 280:815–819 (1979).
Watson R.J., et al., "Herpes Simplex Virus Type–1 Glycoprotein D Gene: Nucleotide Sequence and Expression in *Escherichia Coli*," *Science* 218:381–384 (1982).
Young et al., "Expression of *Plasmodium Falciparum* Circumsporozoite Proteins in *Escherichia Coli* for Potential use in a Human Malaria Vaccine," *Science* 228:958 (1985).

*Primary Examiner*—Michael P. Woodward
*Assistant Examiner*—Mary K. Zeman
*Attorney, Agent, or Firm*—Roberta L. Robins; Alisa A. Harbin; Robert P. Blackburn

[57] ABSTRACT

Novel immunogenic compositions are provided involving viral particles composed at least in part of hybrid proteins of at least a portion of a particle forming protein and one or more polypeptides having at least one epitope of interest. Nucleic acid sequences are employed coding for the hybrid protein which are introduced into a host cell for expression, either by themselves or in combination with other DNA sequences coding for particle forming proteins. Expression of the DNA sequences results in formation of particles which may be isolated and used as immunogens for production of antibodies for diagnostics purposes, passive immunization, vaccination, or other uses.

*Saccharomyces carlsbergensis*, 2150-2-3 (pDC103), was deposited on Sep. 7, 1984, at the ATCC and given ATCC Accession No. 20726. Also, *Saccharomyces cerevisiae* PO17 (pCl/l-MCS29) was deposited at the ATCC on Sep. 5, 1985, and given ATCC Accession No. 20770.

5 Claims, No Drawings

HYBRID PARTICLE IMMUNOGENS

This application is a continuation of U.S. patent application Ser. No. 08/352,989 filed on Dec. 9, 1994, U.S. Pat. No. 5,792,465, which is a continuation of application Ser. No. 08/126,115 filed on Sep. 23, 1993 (abandoned), which is a continuation of application Ser. No. 07/966,291 filed on Oct. 26, 1992 (abandoned), which is a continuation of application Ser. No. 07/128,639 filed on Dec. 4, 1987 (abandoned) which is a divisional of application Ser. No. 06/777,976 filed on Sep. 19, 1985 (now U.S. Pat. No. 4,722,840), which is a continuation-in-part of application Ser. No. 06/650,323 filed on Sep. 12, 1984, now abandoned.

BACKGROUND OF THE INVENTION

1. Field of the Invention

The immune system is an incredibly sophisticated organization of cells, secreted factors and responses for protecting vertebrates against disease caused by pathogens or toxins. The fact that mammals are subject to disease, but survive in most instances, demonstrates both the fallibility of the system and its extraordinary capabilities. The immune system has found wide application for both in vivo and in vitro purposes, where vaccination, passive immunization, and production of antibodies for in vitro diagnostics, histology, cytology, and the like find application. With the advent of monoclonal antibodies, the immune system has seen an extraordinary expansion of its utilization for the production of monoclonal antibodies for a wide variety of purposes, where polyclonal antibodies were inadequate.

The immune system is complex and is not fully understood. The manner in which the immune system recognizes foreign immunogens from host peptides and saccharides has still not been elucidated, but is the subject of extensive investigation. Numerous instances exist where a mammalian host is subjected to foreign proteins, where only a weak or undetectable immune response is obtained. Many vaccines are based on the use of attenuated organisms, which carry with them the possibility of a virulent organism, which can result in infection upon immunization. In many instances, it is desirable to immunize with a surface protein or immunogenic portion thereof, but this is frequently found to be unsatisfactory due to a weak response or failure to produce antibodies to the relevant epitopic site. Many proteins or epitopic sites are found to be weakly immunogenic, so that when injected into a xenogeneic host, little if any neutralizing antibodies are obtained to the site(s) of interest.

It is therefore of great interest to be able to prepare compositions which demonstrate high immunogenicity to an epitopic site of interest. In this manner, one can obtain an enhanced immune response upon vaccination, provide antibodies which will be active in passive immunization and produce antibodies to what are otherwise weakly immunogenic epitopic sites in conventional hosts employed for the production of antibodies. Further, it would be preferable to produce compositions containing epitopic sites from more than one infectious agent. These compositions could then be utilized as polyvalent vaccines, allowing for less expensive, more efficient, and safer immunization regimens.

2. Description of the Relevant Literature

The entire genome of Hepatitis B virus has been cloned in *E. coli* and its nucleotide sequence has been determined (Valenzuela et al., *Nature* (1979) 280:815–819; Valenzuela et al., *Animal Virus Genetics* (1980) pp. 57–70). Hepatitis B surface antigen particles have been synthesized and assembled in the yeast *S. cerevisiae* (Valenzuela et al., *Nature* (1982) 298:347–350). The synthesis and assembly in yeast of Hepatitis B surface antigen particles containing the pre-surface antigen region has been described in copending application Ser. No. 621,756, filed on Jun. 18, 1984, entitled "Hepatitis Surface Antigen Particle Vaccine." The cloning of the Herpes Simplex virus glycoprotein D gene in *E. coli* and the gene nucleotide sequence has been reported (Watson et al., *Science* (1982) 218:381–384). The cloned glycoprotein D gene has been expressed in yeast as reported in copending application Ser. No. 631,669, filed Jul. 17, 1984, entitled, "Improved Expression of Glycoprotein D of Herpes Simplex Virus."

The sequence of the circumsporozoite (CS) protein for the human malarial parasite *Plasmodium falciparum* has been cloned (Dame et el., *Science* (1984) 225:593 and Enea et al. ibid p. 628). CS proteins from *P. falciparum* and *P. Knowlesi* have been expressed in *Escherichia coli* (Young et al., *Science* (1985) 228:958) and yeast (Sharma and Godson, *Science* (1985) 228:879). Also, synthetic peptiedes from the CS protein of *P. falciparum* were found to be immunogenic for mice and rats (Ballou et al., *Science* (1985) 228:996). All of the above relevant disclosures are incorporated herein by reference.

SUMMARY OF THE INVENTION

Novel immunogenic compositions are provided comprising viral particles which include hybrid viral particle forming proteins of a least a portion of a naturally occurring viral particle forming protein and one or more oligopeptides having one or more epitopic sites of interest. The oligopeptides can include antigenic regions from bacteria parasites, different viruses, or other infectious agents. The particles are formed by preparing a nucleic acid sequence coding for the hybrid protein, which is introduced into a host cell for expression, either as the sole particle forming protein or in combination with a nucleic acid sequence encoding one or more different particle forming proteins. The nucleic acid sequence is expressed in the host to produce polypeptides which assemble into particles. The particles can be used as immunogens for the production of antibodies to both the particle forming polypeptide and the epitopic sites of interest. The particles may find use as vaccines, or for the production of isolatable, polyclonal or monoclonal antibodies, which antibodies can be used for passive immunization, in vitro diagnostics, cytology, histology, or other applications.

DESCRIPTION OF THE SPECIFIC EMBODIMENTS

Novel immunogenic compositions are provided for enhanced immunogenicity of one or more predetermined epitopic sites, by employing a polynucleotide fragment coding for one or more polypeptides or oligopeptides having epitopic sites joined in proper reading frame, with or without the presence of an intron, to a nucleic acid sequence coding for at least a portion of a particle forming polypeptide, where the resulting hybrid protein retains the capability of particle formation. Particularly, nucleic acid sequences are employed coding for at least a portion of a viral particle forming polypeptide joined at the 5' terminal region in the direction of transcription of the sense strand to the 3' end in the same orientation of a polynucleotide sequence coding for one or more epitopic sites of interest. The polynucleotide sequence coding for the epitopic sites of interest is not naturally found joined to the sequence coding for the particle forming polypeptide. The resulting hybrid gene which codes for the hybrid protein is joined to transcriptional regulatory and translational initiation and termination signals and introduced into a host under conditions for expression and particle assembly. The assembly may be as a result of the particle formation of solely the hybrid protein or the hybrid protein in conjunction with other particle forming proteins.

As part of the process of packaging, viral genes encoding for capsid proteins are expressed in the host and assemble to form the capsid. The capsid may then be isolated in accordance with conventional ways and used as an immunogen for stimulating the formation of antibodies. The requirements for a particle forming polypeptide to be used in the preparation of a hybrid particle forming protein are that the polypeptide is sufficiently stable in the host cell to result in the formation of capsids; that the polypeptide will automatically assemble into a capsid in the cytoplasm; that the terminus of the particle forming protein or fragment thereof may be modified with one or more different polypeptides (e.g., oligopeptides), whereby the foreign polypeptides are presented at the surface of the particle in a desired antigenic conformation; and the particle forming protein is not cytotoxic in the expression host.

As exemplary of a particle forming protein which can be prepared in a unicellular microorganism host is the Hepatitis B surface antigen (HBsAg), particularly the precursor to the Hepatitis B surface antigen, preS-Hepatitis B surface antigen (preS-HBsAg).

The particle forming protein of the Hepatitis B virus (HBV) may be used in its entirety, may be used as a particle forming fragment thereof, usually having at least about 90% of the amino acid sequence, particularly retaining the N-terminus and desirably including at least a portion of the preS, usually at least about 5%, preferably at least about 25%, where the amino acids may be removed from any portion of the preS portion, usually at the N-terminus. The preS polypeptide has 168 amino acids, and when a fragment is employed it will usually have about 10 to 100 amino acids. The preS portion may involve from about 25 to 75 amino acids, usually from about 35 to 65 amino acids of the naturally occurring preS portion, particularly the C-terminal portion.

The gene for the particle forming protein may be available or may be obtained in accordance with conventional techniques. The genes encoding for HBsAg has been described in Valenzuela et al., 1982, supra, while the precursor preS-HBsAg gene is described in U.S. application Ser. No. 621,756, filed on Jun. 18, 1984, whose relevant disclosure is incorporated herein by reference.

Where the gene coding for the particle forming protein is not available, the protein may be isolated, partially sequenced, and based on the amino acid sequence, DNA probes can be prepared. The virus may then be isolated, as appropriate, fragmented to provide for fragments of from about 5 to 20 kb, and the fragments separated according to molecular weight and screened with the probes for duplex formation. The fragments forming duplexes are then cloned, purified, and may be subcloned to provide for smaller fragments, which are cloned. The subcloned fragments are then separated according to molecular weight and screened again with probes for duplex formation. Those fragments which duplex, may now be used in turn as probes for screening the viral genome, which has been cleaved with mung bean nuclease. This enzyme is found to cleave at about the termini of genes. See McCutchan et al., *Science* (1984) 225:625–628.

Alternatively, the cloned fragments may be sequenced, open reading frame sequences determined and those sequences conforming to known amino acid sequences of the particle forming protein isolated and used to define the structural gene. As appropriate, the various genes may be manipulated to remove portions of the structural gene, to modify specific nucleotides, which may result in a change in or retention of the natural amino acid, which may provide for introduction of a restriction site or other manipulative convenience, or the like.

Superfluous DNA can be removed by restriction, exonuclease digestion, e.g., Bal31, primer repair, in vitro mutagenesis, or other manipulative technique. After each manipulation of the fragments to be used for forming the hybrid sequence, the fragments will be cloned, purified and subjected to the next succeeding manipulation. Depending upon the particular particle forming polypeptide, the hybrid protein may have the epitope of interest at the N-terminal region or C-terminal region. Thus, the DNA sequence coding for the epitope of interest may have the sense strand joined in reading frame either at the 3' or 5' end to the 5' or 3' end respectively of the sense strand of the fragment coding for the particle forming protein.

The sequence coding for the oligopeptides of interest may come from any source, naturally occurring, synthetic or combination thereof, but will not naturally be joined to the particle forming protein. The naturally occurring sequence may be shortened, or otherwise modified to introduce restriction sites, provide for expression host preferred codons, or the like. Generally, the sequence will be one that does not disrupt the capability of the particle forming polypeptide. Typically, the sequence will code for less than about 50 amino acids, often between 10 and 20 amino acids, but may be 5 amino acids or less.

Of particular interest are sequences coding for at least one epitopic site of an oligopeptide, which epitopic site is present on a toxin, or part of a pathogen, such as a surface or membrane protein, secreted protein, envelope protein or capsid protein. Thus, the use of the particles as vaccines would typically involve polypeptides or oligopeptides of interest associated with infectious agents. Such infectious agents would include, by way of example and not of limitation, bacteria both gram-negative and gram-positive; viruses, much as the herpes viruses, the AIDS-associated retrovirus, and the like; parasites, such as the human malarial parasite *Plasmodium falciparum*; etc. When the infectious agent has dominant epitopes or those composed of repeating units, the sequences thereof are preferred for inclusion in the constructs of the present invention. The sequence employed can be manipulated at its terminal by restriction, ligation of adapters or linkers, in vitro mutagenesis, primer repair, or the like, to provide for joining to the sequence coding for the particle forming protein.

Various techniques exist for joining DNA fragments. Frequently, there will be restriction sites proximal to the sites of the intended juncture of the two fragments. In this situation, where the two ends are cohesive and complementary, and the lost codons are not necessary, the two ends can be joined together, where the proper reading frame is established. Alternatively, adapters may be employed, where the adapters restore some or all of the lost nucleotides, providing for the two fragments to be in proper reading frame or providing different nucleotides, which code for amino acids different from the naturally occurring amino acids at the juncture. Conveniently, one of the fragments is cloned on a vector, restricted at the appropriate site and then further manipulated, e.g., by restriction, insertion of an adapter, etc., followed by insertion of the other fragment, followed by cloning of the hybrid sequence.

Once the hybrid sequence has been prepared, it may then be further modified for expression. This will require that the hybrid sequence be joined to transcriptional regulatory and translational signals in proper orientation for expression in the expression host. Either eukaryotes or prokaryotes may be employed as the expression host, either unicellular micro-organisms or mammalian cells. In each instance, there are ample expression vectors available for expression of the hybrid particle forming protein. For prokaryotes, *E. coli, B. subtilis, B. thermophilus*, or the like may be employed. For unicellular eukaryotes, *S. cerevisiae, S. kluveromyces, S. pombe*, or the like, may be employed. Higher mammalian cells include mouse cells, human cells, monkey cells, or the like.

Of particular interest is the expression of the hybrid protein in yeast cells. For expression in yeast cells, various expression vectors may be employed, usually employing the 2$\mu$ replication system, when other than integration of the structural gene is desired. Where integration is desired, the vector may employ an ars for high efficiency of transformation with integration. The vectors will normally have one or more markers for selection in yeast, where the marker may provide prototrophy to an auxotrophic host, resistance to a biocide, e.g., to antibiotics such as G418, tunicamycin or heavy metal, such as copper or zinc, or other selective technique.

The yeast transcriptional regulatory initiation sequences can be derived from a variety of genes, particularly the glycolytic genes, such as alcohol dehydrogenase, glyceraldehyde-3-phosphate dehydrogenase, glucose-6-phosphate dehydrogenase, triosephosphate isomerase, phosphofructokinase, etc., or other genes such as acid phosphatase, beta-actin, alpha-amylase, heat shock proteins, metallothioneins, etc. Any convenient transcriptional termination sequence may be employed which is operative with the transcriptional initiation sequence, conveniently a termination sequence associated with the same gene as the initiation sequence. In addition, where integration is involved, the hybrid gene may be placed in tandem with another gene which allows for amplification, such as a metallothionein gene, e.g., copper chelatin gene, dihydrofolate reductase gene, etc.

In addition to the other sequences, a prokaryotic replication system may also be included, so as to allow cloning at each stage. Various prokaryotic replication systems exist, ColE1, P-1 incompatibility plasmids, R6, such as lambda, etc.

The constructs of the subject invention can be diagrammatically illustrated by the following formula.

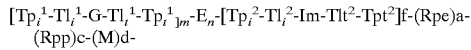

$$[Tp_i^1\text{-}Tl_i^1\text{-}G\text{-}Tl_t^1\text{-}Tp_t^1]_m\text{-}E_n\text{-}[Tp_i^2\text{-}Tl_i^2\text{-}Im\text{-}Tlt^2\text{-}Tpt^2]f\text{-}(Rpe)a\text{-}(Rpp)c\text{-}(M)d\text{-}$$

wherein:

$Tp_i$ intends a regulatory signal for transcriptional initiation;

$Tl_i$ intends the regulatory signal for translational initiation;

$Tl_t$ intends the regulatory sequence for translational termination;

$Tp_t$ intends the regulatory sequence for transcriptional termination;

wherein the superscripts 1 and 2 indicate that the various regulatory sequences may be the same or different, wherein all of the regulatory sequences will be recognized by the same host and be capable of functioning for expression in the same host;

G is a gene having a DNA sequence coding for a product which protects the expression host from stress, such as an antibiotic or heavy metal and results in amplification of the gene and flanking regions, so as to provide for tandem copies of the gene and flanking regions; desirably, the gene and flanking regions which make up the construct will include sequences having homology with the genome of the expression host, so as to enhance the probability of integration into the genome; particular genes of interest include the gene encoding dihydrofolate reductase, the gene coding for kanamycin resistance (G418), the gene coding for tunicamycin resistance and a gene coding for a metallothionein, to provide resistance to heavy metal;

E is an enhancer which enhances the rate of transcription;

Im is the immunogen which has the formula $(Ag_i)_k$-$(prePP)_b$-$Ag_p$ wherein:

$Ag_i$ intends the antigen of interest which provides an epitopic site not naturally joined to $Ag_p$ capable of inducing an immune response for formation of an antibody specific for the epitopic site;

prePP intends a polypeptide which will normally be all or a portion of a naturally occurring N-terminal polypeptide, generally cleaved from a larger polypeptide, usually involving $Ag_p$ and may serve as a link between $Ag_i$ and $Ag_p$;

m, n and b are 0 or 1;

k and f are each 1 or more, typically 2 or 3; and typically, if k is more than 1, then f will be 1, and vice versa.

$Ag_p$ is a particle forming antigen which will be substantially the same as a naturally occurring particle forming antigen or portion thereof, which portion is capable of forming a particle in conjunction with $Ag_i$ and may be derived from any virus which forms a particle in a host and provides for exposure of $Ag_i$ for production of antibodies, particularly the HBsAg antigen;

$Rp_e$ and $Rp_p$ are replication systems for eukaryotic and prokaryotic cells;

a and c are 0 or 1;

M is a marker providing for a selection in a cloning or expression host, where the markers may be the same or different and include resistance to biocides, such as antibiotics, heavy metals, or the like; providing prototrophy to an auxotrophic host; or the like;

d is from 0 to 5, usually 1 to 4;

the sequences in brackets give an indication of the preferred order of appearance of the DNA sequences, while those portions outside the brackets may be in any order.

The various sequences may be joined in accordance with conventional techniques. Where restriction sites are available outside of functional sequences such as regulatory sequences, coding sequences, or the like, the two sequences may be joined, where the restriction sites are complementary or linkers may be employed for joining the two sequences. Usually, the construct will be built up incrementally, usually employing cloning vectors, where fragments are inserted into the cloning vector stepwise, cloned and the vectors isolated and purified. Where restriction sites are not available outside of functional sequences or inconveniently situated in relation to functional sequences, adapters can be used, which recreate all or a portion of the functional sequence and join together two functional sequences in proper orientation. Alternatively, convenient restriction sites can be created by mutagenesis of the sequences and such sites can be used in the joining procedure. Various techniques for improving the efficiency with which sequences are joined together include alkaline phosphatase treatment of one sequence; filling in of sequences to provide for blunt end ligation, tailing, or the like.

Once the construct has been prepared having the necessary functional sequences, the expression construct may be introduced into a compatible host by any convenient technique, such as transformation, e.g., polyethylene glycol precipitation, conjugation, transfection, transduction, or the like. The recipient cells may then be grown in an appropriate nutrient medium to a desired density, the cells harvested, a lysate prepared by any convenient means, e.g., agitation with glass beads, and the desired protein harvested.

The protein of the subject invention will naturally aggregate to form particles in the expression host. The particles may be enveloped having a lipid membrane coat, which may or may not include membrane proteins encoded for by the virus. Alternatively, the particles may not include the lipid membrane or the membrane may be present initially or may be removed, in whole or in part.

The particles may be used as immunogens in a wide variety of ways. The particles may be isolated by affinity chromatography employing a column which recognizes either or both of the antigens present, or alternatively, separations can be employed using density gradients, gel filtrations and the like. The techniques may be used individually or in combination.

Any of the conventional methods for administration of a dead virus vaccine are applicable. These include applications on a solid physiologically acceptable base or in a physiologically acceptable dispersion, parenterally, by injection, or the like. The dosage of the vaccine will depend on the route of administration and will vary according to the size of the host. Because the vaccine will have few, if any, side effects, relatively large doses may be used without injury to the host. Normally, the amount of the vaccine will be from about 1 μg to 20 mg per kilogram of host, more usually from about 5 μg to 20 μg given subcutaneously or intramuscularly, after mixing with an appropriate carrier or an adjuvant to enhance immunization with the vaccine.

Various methods of achieving adjuvant effect for the vaccine include use of agents such as aluminum hydroxide or phosphate (alum), commonly used as a 0.05 to 0.1% solution in phosphate buffered saline, admixture with synthetic polymers of sugars (Carbopol), used as a 0.25% solution mixture with bacterial cells such as C. parvum or endotoxins or lipopolysaccharide components of Gram-negative bacteria, emulsion in physiologically acceptable oil vehicles, such as mannide mono-oleate (Aracel A) or emulsion with a 20% solution of a perfluorocarbon (Fluosol-DA) used as a blood substitute.

The amount of the adjuvant which is employed will vary widely depending upon the nature of the adjuvant, generally ranging from 0.1 to 100 times the weight of the immunogen, more usually from about 1 to 10 times.

In many instances it will be desirable to have multiple administrations of the vaccine, usually not exceeding six vaccinations, more usually not exceeding four vaccinations, and preferably one or more, usually about three vaccinations. The vaccinations will normally be at from 2 to 12 week intervals, more usually from 3 to 5 week intervals, with optional periodic boosters at intervals of 1 to 5 years. The course of the immunization may be followed by assays for antibodies to the antigen of interest.

The subject particles can also be used in assays for detecting the presence of antibodies to the antigen of interest. In use in assays, the individual protein or particle will normally be labeled with one of a variety of labels which find use in assays. These labels have been extensively reported in the patent and technical literature and include radionuclides, fluorescers, chemiluminescers, enzymes, enzyme substrates, small molecules, and the like.

The particle of the subject invention may be used for the production of antibodies in various mammalian hosts, e.g., murine, bovine, ovine, lagomorpha, human, etc. The antibodies can then be used in immunoassays for the detection of the presence of the antigen of interest. Alternatively, the antibodies can be used for passive immunization and may be administered in vivo in conventional ways to a mammalian host.

The subject particles can be used in conventional ways to produce antisera or monoclonal antibodies (Kohler and Milstein, *Nature* (1975) 256:495–497, which is incorporated herein by reference). For monoclonal antibodies, the hybridomas may be grown in culture or injected intraperitoneally for formation of ascites fluid or into the blood stream of an allogeneic host or immunocompromised host. The antibodies may then be isolated in conventional ways.

The following examples are offered by way of illustration and not by way of limitation.

EXPERIMENTAL

TE 10 mM Tris-HCl, pH 8.0, 1 mM EDTA
EDTA Ethylene-diamino-tetracetic-acid
PBS Phosphate buffered saline
SDS Sodium dodecyl sulfate
BSA Bovine-serum albumin
ADH Alcohol dehydrogenase
GAPDH Glyceraldehyde 3-phosphate dehydrogenase
HSV Herpes simplex virus
gD Glycoprotein D
HBV Hepatitis B virus
HBsAg Hepatitis B surface antigen
pre-S Pre-surface
HRP Horseradish peroxidase
kbp kilobase pairs All DNA manipulations were done according to standard procedures. See *Molecular Cloning*, T. Maniatis et al., Cold Spring Harbor Lab., New York, 1982. Enzymes used in cloning were obtained either from New England Biolabs or Bethesda Research Laboratories and employed according to the supplier's directions. Yeast were transformed and grown using a variety of media including selective medium (yeast nitrogen base without leucine); YEPD medium, containing 1% (w/v) yeast extract, 2% (w/v) peptone and 2% (w/v) glucose, and others as appropriate and/or detailed below. In the case of plating, medium contained 2% (w/v) agar and for transformation, 3% top agar. Medium compositions have been described by Sherman et al., 1979, *Methods in yeast genetics: A Laboratory Manual*, Cold Spring Harbor Lab., New York.

1. Description of Vectors Used in the Construction of the Yeast Expression Vector for the Hybrid Antigen (preS-HBsAg-gD and preS-HBsAg-CS)

1a. Plasmid pCl/l.
See EPO 83/306507.1, which relevant part is incorporated herein by reference.

1b. Plasmid pYHS119.
This vector contains a partial gD gene in a glyceraldehyde-3-phosphate dehydrogenase (GAPDH) expression cassette cloned into the-BamHI site of pCl/l (described above). The cloned partial gD gene contains two deletions of 600 bp and 2400 bp in the 5' and 3' end coding regions, respectively. These deletions comprise most of the signal sequence (5') and all of the anchor sequence (3') coding regions. To construct pYHS119 two fragments were obtained:

(i) An NcoI-SalI digested vector (6.8 kbp) comprising pBR322 sequences, the GAPDH promoter plus the first seven codons of the GAPDH structural gene and the GAPDH terminator. This vector was prepared by NcoI digestion of pUH28 (described below), followed by a partial digestion with SalI and purification by gel electrophoresis.

(ii) An NcoI-(NarI)SalI fragment (873 bp) containing a partial gD gene. This fragment was obtained as follows: plasmid pYHS115 (described below) was digested with NcoI and SalI, the resulting 1430 bp fragment containing the gD gene was purified by gel electrophoresis and subsequently digested with NarI. The 873 bp NcoI-NarI fragment was isolated by gel electrophoresis. A synthetic adapter of the following sequence:

```
5'-CGCCGCAAATCTAC-3'
    GGCGTTTAGATCAGCT
    ↑              ↑
   NarI           SalI
``` which provides complementary nucleotides to the NarI 5' overhang, 3 codons in reading frame, a stop codon and a 5' overhang of SalI, was ligated to the 873 bp NcoI-NarI fragment and then digested with SalI to yield the NcoI-(NarI)SalI fragments.

These two fragments were ligated together to yield a pBR322 derived vector which contains a partial gD gene fused in reading frame to the seven first codons of the GAPDH gene, flanked by the GAPDH promoter at its 5' end and by the GAPDH terminator at its 3' end. The gD expression cassette was obtained by digesting this plasmid with BamHI and purifying a 3.4 kbp fragment by gel electrophoresis. This fragment was ligated to BamHI digested, alkaline phosphatase treated pCl/1 (previously described), to produce pYHS119.

1c. Construction of plasmid pUH28.

Plasmid pUH28 contains the coding and 3' non-coding regions of the Hepatitis B surface antigen (HBsAg) gene fused in incorrect reading frame to the first 7 codons of the GAPDH structural gene. This fusion is flanked at its 5' end by the GAPDH promoter and at its 3' end by part of the GAPDH coding region followed by the GAPDH terminator. This plasmid was constructed so as to have an NcoI site at the 3' end of the first 7 codons of the GAPDH structural gene with the following sequence:

```
              Met
5'-AAACAAAATGGTTAGAGTTGCTAATTCC-3'

TTTGTTTACCAATCTCAACGATTAAGGGTAC
   3'GAPDH     5'GAPDH        NcoI site
   promoter    coding region
```

When this NcoI end is ligated to the partial gD fragment (see construction of pYHS119, described above) the correct reading frame for the gD protein is regenerated. The SalI site used in the preparation of fragment (i) (described above) is at the 5' region of the GAPDH terminator. Therefore, a deletion of the HBsAg coding plus non-coding regions and GAPDH coding region was obtained by digesting pUH28 with NcoI and partially with SalI.

The construction of pUH28 involves cloning of a fragment that contains the HBsAg coding and 607 bp of 3' non-coding region prepared from pHBS5-3 Hae2-1 (described below) into the GAPDH containing vector pGAP$_2^1$ (described below). To prepare the fragment, pHBS5-3 Hae2-1 was linearized by PstI digestion, partially digested with NcoI and a PstI-NcoI fragment of 1.9 kbp containing pBR322 sequences, HBsAg coding and 3' sequences was purified by gel electrophoresis. This fragment was subsequently digested with EcoRI and a 1.2 kbp NcoI-EcoRI fragment containing the HBsAg coding and 3' non-coding regions was purified by gel electrophoresis. Plasmid pGAP$_2^1$ was linearized with XbaI and treated with Bal31 to remove approximately 100 bp. The plasmid was subsequently digested with NcoI and a vector fragment of about 9 kbp was purified by gel electrophoresis. The NcoI ends of the vector and the 1.2 kbp NcoI-EcoRI fragment encoding HBsAg were ligated The recessed end was filled in with Klenow and the resulting blunt end was ligated to the blunt end of the vector obtained by Bal31 digestion to produce pUH28.

pHBS5-3 Hae2-1 is a plasmid that contains the HBsAg coding region and 607 bp of the 3' flanking sequence. This plasmid is a derivative of pHBS5-3 which contains the same insert but only 128bp of 3' untranslated region instead of 607 bp. Plasmid pHBSS-3 has been previously described in copending application, Ser. No. 609,540, filed May 11, 1984, (pp. 13–14). pHBS5-3 Hae2-1 was constructed as follows. The HBV genome (3.2 kb) was excised from pHB-3200 (Valenzuela et al., *Nature* (1979) 280:815–819) by restriction digestion with EcoRI. The 3.2 kbp fragment was purified by gel electrophoresis and was recircularized by ligation of the EcoRI sticky ends. This closed HBV genome was digested with HaeII, which cuts in the 3' non-coding region. Recessed ends were filled in with Klenow fragment and HindIII linkers were ligated. The DNA was cut with HindIII and subsequently with XbaI, which has a single site in the HBsAg coding region. A 1.2 kbp XbaI-HindIII fragment containing 586 base pairs of the coding sequence of HBsAg and 607 base pairs of the 3' non-coding region was isolated by gel electrophoresis. This fragment was cloned into pHBS5-3 previously cut with XbaI and HindIII and treated with alkaline phosphatase, to yield pHBS5-3 Hae2-1.

pGAP-2 is a pBR322 derived vector which contains a BamHI insert that has the GAPDH coding sequence, 5' and 3' flanking regions. There are two XbaI sites in this plasmid: one in the coding region and one in the 3' flanking sequences. pGAP-2' is a derivative of pGAP-2 in which the XbaI site present in the 3' flanking region has been eliminated. For this purpose, 50 μg of pGAP-2 were partially digested with XbaI, treated with Bal31 to remove 25 base pairs per end, and ligated. The plasmids were used to transform *E. coli* HB101 and the transformants were selected for loss of the XbaI site in the 3' flanking region.

1d. Construction of pYHS115.

Plasmid pYHS115 contains the gD gene in a glyceraldehyde-3-phosphate dehydrogenase (GAPDH) expression cassette cloned into the BamHI site of pCl/1 (described above).

The GAPDH expression cassette was constructed as follows. Three fragments were prepared (as described in detail below):

(a) A BamHI-HindIII fragment (1407 bp) containing 346 bp of pBR322 and 1061 bp of the GAPDH promoter;

(b) A HindIII-SalI fragment (1430 bp) containing the gD gene, and (c) A SalI-BamHI fragment (900 bp) containing the GAPDH terminator.

These fragments were ligated together and the mixture was digested with BamHI. The 3.7 kbp resulting cassette was isolated by gel electrophoresis and ligated to BamHI cut, alkaline phosphatase-treated pCl/1.

Fragment (a) was prepared by completely digesting pGAP347 (described below) with BamHI followed by partial digestion with HindIII. The resulting 1407 bp fragment containing 346 bp of pBR322 and 1061 bp of the GAPDH promoter was isolated by gel electrophoresis.

Plasmid pGAP347 which contains the GAPDH promoter (1061 bp) cloned into pBR322 was constructed (see copending application Ser. No. 468,589, filed Feb. 22, 1983):

PolyA+ RNA was isolated from *S. cerevisiae* yeast strain A364A. Double-stranded cDNA was synthesized using AMV reverse transcriptase and *E. coli* DNA polymerase I. Poly-dC-tails were added to the double-stranded cDNA molecule using deoxynucleotide terminal transferase. Poly-dC-tailed cDNA was annealed to poly-dG-tailed pBR322 and used to transform *E. coli* HB101. One thousand transformants were screened by colony hybridization to labeled PolyA+ RNA, and a subset further examined by restriction endonuclease mapping, and DNA sequencing. Three clones containing GAPDH sequences were isolated from the pool. One clone (pcGAP-9) contained an insert of about 1200 base pairs and was used for further work.

A yeast gene library was prepared by inserting fragments obtained after partial digestion of total yeast DNA with restriction endonuclease Sau3A in lambda phage Charon 28, according to Blattner et al., *Science* (1977) 196:161–169. Several fragments containing yeast GAPDH coding sequences were isolated by screening the phage library with labeled DNA from pcGAP-9. The yeast GAPDH gene of one of these clones was subcloned in pBR322 as a 2.1 kbp HindIII fragment (pGAP-1). The GAPDH promoter region was isolated from these clones. A HhaI-HindIII fragment of about 350 bp containing the 31 portion of the promoter was obtained by: (a) digestion of pGAP-1 with HinfI to generate an approximately 500 bp segment which includes the 3' part of the promoter and a region encoding the N-terminal amino acids of GAPDH; (b) resection with Bal31 to yield a 400 bp fragment lacking the GAPDH coding region (3'-terminus one base upstream from the ATG initiator codon); (c) addition of HindIII linkers; and (d) cleavage with HhaI to yield a 350 bp HhaI-HindIII fragment. A second HindIII-HhaI fragment of about 700 bp containing the 5' portion of the promoter was isolated from pGAP-1, ligated to the 350 bp HhaI-HindIII fragment and treated with HindIII. The resulting 1061 bp HindIII fragment was isolated by gel electrophoresis and cloned in HindIII digested, alkaline phosphatase treated pBR322 to produce pGAP347.

Fragment (b) was obtained as follows. Clone H, isolated from the HSV-1 Patton library was digested with SacI. A 2.9 kbp SacI fragment was purified by gel electrophoresis and subsequently digested with HindIII and NruI. The 1430 bp HindIII-NruI fragment containing the gD gene was purified by gel electrophoresis, ligated to NruI-SalI adapters of the following sequence:

```
5'-TGATAAG-3'
   ACTATTCAGCT
``` and digested with SalI.

Fragment (c) was obtained as follows. A 900 bp fragment containing the GAPDH terminator was obtained by BamHI and SalI digestion of pUH28 (described above) and purification by gel electrophoresis.

1e. Construction of plasmid pDC101.

This vector contains the preS-HBsAg gene (including 55 codons of the pre-S region) in a GAPDH expression cassette cloned into the BamHI site of a pBR322 derivative (pBRΔRl-Sal, described below). To construct this plasmid, the 3.2 kbp BamHI expression cassette was excised from pHBpreSGAP347/19T (described below) by BamHI digestion. After purification through gel electrophoresis, the 3.2 kbp BamHI fragment was ligated to BamHI-digested, alkaline phosphatase treated pBRΔRl-Sal and cloned in *E. coli* to yield pDC101.

1f. Construction of plasmid PBRΔRl-Sal.

This plasmid is a derivative of pBR322 in which the region between the EcoRI site and SalI site has been deleted and a BamHI site has been created. This plasmid was constructed by digesting pBR322 with EcoRI and SalI. After filling in the overhanging ends with the Klenow fragment, BamHI linkers were ligated, followed by BamHI digestion and the vector was recircularized and cloned to yield pBRΔRl-Sal, which contains no EcoRI site.

1g. Construction of pHBpreSGAP347/19T.

A cassette containing the yeast glyceraldehyde-3-phosphate dehydrogenase (GAPDH) promoter region, the pre-S- HBV region comprising 165 bp encoding 55 amino acids; the coding sequence for the surface antigen (HBsAg) gene in reading frame with pre-surface (pre-S) sequences; and the GAPDH terminator region, was prepared by ligating the following four fragments: a) a 1407 bp BamHI-HindIII fragment that contains the GAPDH promoter; b) a 14 bp HindIII-EcoRI adapter molecule coding for the first three amino acids of the pre-S region; c) a 250 bp EcoRI-XbaI fragment encoding a segment of the pre-S region (52 amino acids) and the first 32 amino acids of the HBsAg N-terminal region, and d) an approximately 1580 bp XbaI-BamHI fragment containing sAg coding region and the GAPDH terminator.

These four fragments were ligated in steps as follows: 4 picomoles of fragment a (GAPDH promoter) were ligated to 260 picomoles of phosphorylated fragment b (14bp synthetic adapter) in the presence of 10 units of T4 DNA ligase. The product (fragment a-b) was separated from an excess of adapter molecules by preparative gel electrophoresis. Approximately 1.5 picomole of isolated fragment a-b was ligated to -1.5 picomoles of fragment c, a 250 bp EcoRI-XbaI pre-S and HBsAg N-terminal region in the presence of 10 units of T4 DNA ligase. Approximately 1 picomole of the product (fragment a-b-c) was ligated to 1 picomole of fragment d (1580 bp XbaI-BamHI, HBsAg C-terminal region and GAPDH terminator) and to 0.01 picomole of BamHI-digested yeast vector pCl/l in the presence of 5 units of T4 DNA ligase. A plasmid containing the cassette cloned in pCl/l was isolated after transformation of *E. coli* HB101. This plasmid was named pHBpreSGAP347/19T. The strategy followed to obtain fragments a, b, c and d is described below.

Fragment a) A 1407 bp BamHI-HindIII fragment containing 346 bp of pBR322 and a 1061 bp of the GAPDH promoter was prepared by digesting 50 μg of plasmid pHBS56-GAP347/33 (described below) with BamHI and HindIII (10 units each). The fragment was isolated by preparative gel electrophoresis in 1% agarose.

Plasmid vector pHBS-56GAP347/33, which contains HBsAg under control of the GAPDH promoter and the ADH terminator was constructed as follows. Total digestion of pGAP-347 (previously described) with SphI followed by partial digestion with HindIII yielded an approximately 1700 bp SphI-HindIII fragment having about 1060 bp which included the GAPDH promoter and about 530 bp of pBR322. The 1700 bp SphI-HindIII GAPDH promoter fragment was ligated with the 840 bp HindIII-HindIII fragment (containing the HBsAg coding region, 26 bases of 5' non-coding region and 128 bp of 31 non-coding region, obtained from pHBS-56, described below) and then with the 350 bp HindIII-SphI fragment containing the ADH-1 termination region (isolated from pHBS-56). The 2,900 bp SphI expression cassette was isolated and cloned in pHBS-56 previously digested with SphI. The resulting plasmid (pHBS-56GAP347/33) in which the promoter, gene and termination regions were in the proper orientations was isolated.

Plasmid pHBS56 which contains the HBsAg gene under regulation of the ADH promoter and terminator, was obtained as follows: A TagI-HpaI fragment obtained from the HBsAg coding region which included 26 bp of the pre-S region, 681 bp of the sAg region and 128 bp of the 3'-untranslated region (Valenzuela et al., Nature (1979) 280:815–819), was ligated to EcoRI linkers and cloned at the EcoRI site in pBR322. The EcoRI linkers have the sequence GGAATTCC. The plasmid pHBS5 was thus obtained.

The HBsAg-DNA segment of pHBS5 was excised by EcoRI digestion, blunt-ended with the Klenow fragment and joined at both ends with HindIII linkers of the following sequence CAAGCTTG. After digestion with HindIII, the HBsAg fragment was inserted into the HindIII site of the plasmid pADHS (described below) which had been digested at the HindIII site intermediate the ADHl promoter and terminator sequence. A plasmid with the HBsAg gene in the correct orientation as determined by restriction analysis was designated pHBS22. pHBS22 was digested with SphI to obtain a fragment of about 1500 bp containing the HBsAg expression cassette and inserted into SphI digested pCl/l to provide pHBSS6.

Plasmid pADH5 contains 1500 bp ADHl promoter fragment terminating at position -9 (Hitzeman et al., Nature (1981) 293:717) joined with a HindIII site to an approximately 450 bp terminator unit from nucleotides 913 to 1368, cloned into the BamHI site of the vector YEp13 (Broach and Hicks, Gene (1979) 8:121).

Fragment b) A 14 bp HindIII-EcoRI adapter molecule coding for the first three amino acids of the pre-S region (met-glu-trp) and including the five additional bases for the restriction sites was obtained by chemical synthesis

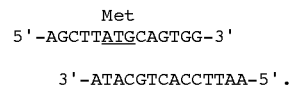

3'-ATACGTCACCTTAA-5'.

Fragment c) A 250 bp EcoRI-XbaI fragment encoding a segment of the pre-S region (52 amino acids) and the first 32 amino acids of the (HBsAg) N-terminal region was obtained by digestion of plasmid pHBV-3200 (50 µg) (Valenzuela et al., Nature (1979) 280:815–819) with the enzymes EcoRI and XbaI (10 units each) and isolated by preparative gel electrophoresis in 6% polyacrylamide.

Fragment d) An approximately 1580 bp XbaI-BamHI fragment containing about 680 bp coding for the remaining C-terminal region of the HBsAg protein (194 amino acids) and 3' HBsAg non-coding region and approximately 900 bp corresponding to the GAPDH terminator region. This fragment was obtained by digesting (50 µg) of the plasmid pHBS70-7Δ (described below) with XbaI and BamHI (10 units each) and the resulting 1580 bp fragment isolated by preparative gel electrophoresis.

Plasmid pHBS70-7Δ is a pCl/l derivative which contains a GAPDH expression cassette for the HBsAg gene cloned into a BamHI site. This cassette was obtained from plasmid pUH-7Δ, a pBR322 derivative which was constructed from pUH7, as follows.

Plasmid pUH7 contains the coding and 3' non-coding region of HBsAg gene flanked at its 5' end by the GAPDH promoter and at its 3' end by part of the GAPDH coding region followed by the GAPDH terminator. This plasmid is almost identical to pUH28 (described previously), the only difference being that pUH7 does not contain the seven first codons of the GAPDH structural gene present in pUH28. Plasmid pUH7 was constructed as pUH-28, the only difference residing in the extent of the Bal31 resection of pGAP$_2$ so that in pUH7 all nucleotides corresponding to the first codons of the GAPDH structural gene were removed by Bal31.

pUH-7Δ is a plasmid derived from pUH7 in which part of the 3' non-coding region of the HBsAg gene and the coding region of GAPDH gene have been deleted. For this construction, two fragments were prepared. The first contains pBR322 sequences and the GAPDH promoter and terminator sequences. This fragment was obtained by digestion of pUH7 with NcoI, followed by a partial digestion with SalI. The NcoI-SalI vector band (approximately 7 kbp) was purified by gel electrophoresis. The second fragment containing the HBsAg coding region with 128 base pairs of 3' untranslated region was obtained by NcoI-HpaI digestion of pUH7. The 0.8 kbp fragment was isolated by gel purification. Both fragments were ligated through their NcoI sticky ends, the recessed ends were filled in with the Klenow fragment and the resulting blunt ends ligated to yield pUH-7Δ.

2. Preparation of Immune Sera and Antibodies for Immunoassays

2a. Rabbit serum against HSV1 glycoproteins.

HSV1 glycoproteins were prepared by affinity chromatography of HSV1 with a lentil lectin column. The glycoprotein mixture was used to immunize rabbits.

2b. Rabbit antibodies against HSV1 glycoproteins.

The serum against HSV1 glycoproteins (obtained as in a.) was adsorbed to HSV1 glycoproteins bound to a lentil lectin column. The adsorbed material was subsequently eluted to yield purified antibodies against HSV1 glycoproteins.

2c. Monoclonal antibody against HBsAg (3A11).

HBsAg was produced by genetically engineered yeast as described by Valenzuela et al. (Nature (1982) 298:347–350). This antigen was used to prepare mouse monoclonal antibodies following conventional procedures (Kohler and Milstein, Nature (1975) 256:495–497).

2d. Monoclonal antibody against CS peptides (2A–10).

Monoclonal antibodies against synthetic CS peptides were obtained from Dr. V. Nussenzweig, New York University.

3. Immunoassays

3a. Capture of hybrid antigen with anti-HSV1 glycoprotein coated bead and color development with anti-HBsAg antibody coupled to horseradish peroxidase (HRP).

Polystyrene beads coated with antibody against HSV1 glycoproteins were incubated with different dilutions of yeast extracts (or controls) in microtiter wells for 2 hr at 42° C. During incubation, gD antigen should bind to the solid phase antibody. After washing the beads to remove unbound material, a second antibody against HBsAg conjugated with HRP (from Abbott Auzyme® kit) was incubated with the antibody antigen complexes on the beads for 2 hr at room temperature and overnight at 4° C. An antibody-antigen-antibody sandwich should be formed with depends upon the antigen molecules containing both antigen determinants (gD and HBsAg). Beads were washed to remove unbound conjugates. The peroxidase activity (which is proportional to the amount of HBsAg) was assayed by a colorimetric method using o-phenylenediamine (OPD, Abbott) and the color development was determined by absorbance at 492–600 nm. Within limits, the greater the amount of antigen in the sample, the higher the absorbance at 492–600 nm. Results are expressed as the total number of OD$_{492-600}$ units per ml of yeast extract.

3b. Capture of hybrid antigen with anti-HBsAg coated bead and color development with HRP conjugated goat anti-rabbit antibody bound to rabbit anti-HSV1 glycoprotein antibody.

Beads coated with guinea pig antibodies against HBsAg (from the Abbott Auzyme® kit) were incubated with yeast extracts (or controls) for 2 hr at 42° C. After washing with water, a 1/200 dilution of the second rabbit antibody against HSV1-glycoprotein was added. Incubation was carried out for 2 hr at room temperature followed by incubation overnight at 4° C. After washing with water, a third peroxidase conjugated goat anti-rabbit antibody was added, and incubation was continued for 1 hr at room temperature. Peroxidase activity was determined as above and color development was measured at 492–600 nm.

3c. HBsAg ELISA assay

Beads coated with guinea pig antibodies against HBsAg (from the Abbott-Auzyme® kit) were incubated with yeast extracts (or controls) for 2 hr at 42° C. After washing with water, a second peroxidase conjugated, goat-anti guinea pig antibody was added, and incubation was continued for 1 hr at room temperature. Peroxidase activity was determined as above and color development was measured at 492–600 nm.

4. Western Analysis

Transformed yeast cells were electrophoresed on 10% polyacrylamide gels (Laemmli, *Nature* (1970) 277:680) and proteins were subsequently electroblotted onto nitrocellulose filters (Towbin et al., *Proc. Natl. Acad. Sci. USA* (1979) 76:3450). Two identical filters were blotted. One filter was preincubated for one hour with 10% goat serum in PBS and subsequently treated for 12 hr at 4° C. with rabbit anti-HSV1 glycoproteins antiserum or with monoclonal antibody (2A-10) against CS peptides. The filter was washed with 5% goat serum in PBS and a second goat anti-rabbit or anti-mouse antibody conjugated with horseradish peroxidase (Boehringer-Mannheim) was added. Finally the filter was incubated with horseradish peroxidase color development reagent (Bio-Rad) and washed.

The second filter was washed for 1 hr with 0.5% gelatin in PBS and subsequently incubated with the monoclonal antibody (3A11) against HBsAg prepared as previously described for 12 hr at room temperature. The filter was washed with PBS and a second goat anti-mouse antibody conjugated with horseradish peroxidase (Boehringer-Mannheim) was added. Finally the filter was incubated with horseradish peroxidase color development reagent (Bio-Rad) and washed.

RESULTS

1. Construction of pDC103, An Expression Vector for the Hybrid Antigen (preS-HBsAg-gD)

The fragment containing the gD gene was cloned into a single EcoRI site present in the pre-S region of plasmid pDC101 (previously described). The EcoRI site spans codons 3 and 4 of this region. The preparation of the fragment containing the gD gene, the linearization and phosphatase treatment of the vector pDC101, the ligation of gD fragment and vector, and the transformation of *E. coli* HB101 are described below.

1a. Linearization and phosphatase treatment of pDC101.

Ten µg of pDC101 were linearized with EcoRI, which cuts within the third and fourth codons of the pre-S region. The linearized plasmid was treated with 38 units of calf intestine phosphatase (Boehringer) for 45 min at 37° C. The reaction was stopped by adding EDTA and SDS to final concentrations of 20 mM and 0.5%, respectively, and heating for 10 min at 65° C. The reaction mix was extracted with phenol:chloroform:isoamyl alcohol (25:24:1), the aqueous phase was passed through a CL6B column to remove SDS, and concentrated to 60 µl with butanol.

This sample was loaded onto a 1% preparative agarose gel and the 6930 bp band was electroeluted. The electroelution mix was concentrated with butanol, extracted with phenol:chloroform:isoamyl alcohol (25:24:1) and precipitated with ethanol. The linearized and phosphatase treated vector was resuspended in TE at a concentration of approximately 50 ng/µl.

1b. Preparation of the fragment containing gD gene.

The gD containing fragment was obtained from pYHS119 (previously described). For this purpose, 10 µg of pYHS119 were digested with 100 units each of BamHI and NcoI in a 300 µl reaction. After incubation for 3 hr at 37° C., the reaction mixture was loaded onto a preparative 1% agarose gel and the 1788 bp BamHI-NcoI fragment containing the gD fragment and GAPDH terminator was electroeluted from the gel. After concentration with butanol, the electroeluted DNA fragment was extracted with phenol:chloroform:isoamyl alcohol (25:24:1), precipitated with ethanol and resuspended in TE at a concentration of 50 ng/µl.

Approximately 2.5 µg of the 1788 bp fragments were digested with 30 units of NarI which cuts at the 3' end of the gD gene producing two bands (888 bp and 900 bp for the fragments containing gD and GAPDH terminator, respectively). The reaction mixture was extracted with phenol:chloroform:isoamyl alcohol (25:24:1) and was precipitated with ethanol. The pellet was resuspended in 20 µl of TE.

An EcoRI-NcoI adapter having the following sequence was synthesized:

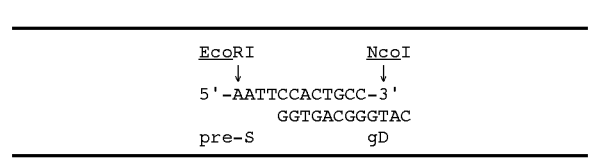

This adapter regenerates the EcoRI and NcoI sites when ligated to pDC101 vector and gD fragment, respectively. It also provides for codons 4 through 7 of the pre-S region and the first codon of the gD fragment. A second adapter, having the following sequence, was synthesized:

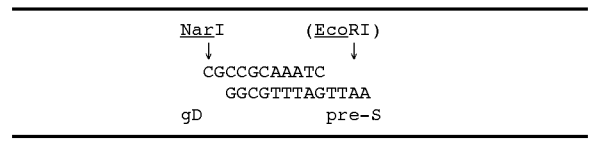

This adapter NarI-(EcoRI) regenerates the NarI site but not the EcoRI site when ligated to pDC101 vector and gD fragment, respectively. It also provides for the last three codons of the gD fragment and for the eighth codon of the pre-S gene.

Both adapters were ligated to the 880 NcoI-NarI fragment containing gD. Ligation was carried out for 17 hr at 14° C. The mixture was then electrophoresed in a 1% agarose gel, and the band in the region between 873 bp and 1078 bp (according to Øx/HaeIII MW standards) was electroeluted. The DNA solution was concentrated with butanol, extracted with phenol:chloroform:isoamyl alcohol (25:24:1) and precipitated with ethanol. The pellet was resuspended in water (30 µl).

1c. Ligation and transformation of *E. coli* HB101.

The purified gD fragment (with ligated adapters) was kinased and ligated to EcoRI linearized, alkaline phosphatase treated pDC101. Ligation was carried out for 2.5 hr at room temperature. The reaction mixture was precipitated with ethanol, resuspended in water and used to transform *E. coli* HB101. Plasmid pDC102 was thus obtained.

1d. Construction of pDC103 by cloning of BamHI cassette from pDC102 into pCl/l.

Plasmid pDC102 was partially digested with BamHI. The resulting 4203 bp fragment containing the hybrid antigen under the control of the CAPDH promoter and terminator, was purified by gel electrophoresis and ligated to BamHI digested, alkaline phosphatase treated pCl/1 (described previously). Ligation was carried out for 3 hr at room temperature. The reaction mixture was precipitated with ethanol, resuspended in water and used to transform *E. coli* HB101. Plasmid pDC103 was thus obtained.

2. Demonstration That Herpes Simplex Virus gD Epitopes and HBsAg Epitopes Are Present in a Fusion Protein 2a. Immunoassays.

To determine whether HSV gD and HBsAg epitopes were present in the same molecule, yeast lysates of cells transformed with pDC103 or with pHBpreSGAP347/19T (control plasmid, described previously) were tested using each of the two immunoassays previously described.

Plasmid pDC103 or pHBpreSGAP347/19T were used to transform *Saccharomyces carlsbergensis* strain 2150-2-3 (Mat a, ade 1, leu 2-64, cir°) following the procedure of Hinnen et al., *Proc. Natl. Acad. Sci. USA* (1978) 75:1929–1933. Transformants were selected on leu-plates.

Single transformant colonies were inoculated into 2.5 ml of selective leu-medium and were grown for 24 hr at 30° C. An aliquot of 0.5 ml of this saturated culture was inoculated into 50 ml of YEPD containing 0.002% adenine and grown to an $OD_{650}$ 6 to 10. Cell free lysates were prepared by agitation with glass beads in lysis buffer (10 mM $NaPO_4$, pH 7.5, 0.1% Triton X-100) and removal of cell debris by centrifugation. Lysates were diluted in assay buffer (50 mM $NaPO_4$, pH 7.0, 1% BSA) and several dilutions were tested.

Table 1 details the results obtained in the sandwich assay using the immobilized anti-HSV1 glycoprotein antibody to capture the antigen and a second soluble anti-HBsAg antibody conjugated with HRP. Color development is proportional to the HBsAg epitopes present in the antigen bound to the beads coated with anti-HSV1 glycoprotein antibody. As Table 1 shows, yeast lysates from transformants harboring pDC103 contained a hybrid antigen capable of forming a complex with both the immobilized and the soluble antibodies while control lysates from cells carrying the control plasmid which produce HBsAg did not have such capability. These results indicate that both HBsAg and gD epitopes were present in the same molecules in lysates from pDC103 transformants.

TABLE 1

HBsAg epitopes present in antigen bound to immobilized anti-HSV1 glycoprotein antibody.

| Lysate dilution | μl lysate in assay | Absorbance (492-600 nm units/ml) | |
|---|---|---|---|
| | | control lysate (pHBpreSGAP347/19T) | pDC103 lysate |
| 1:100 | 2 μl | 0.045 | 0.058 |
| 1:100 | 5 μl | 0.076 | 0.071 |
| 1:100 | 10 μl | 0.071 | 0.109 |
| 1:100 | 20 μl | 0.068 | 0.143 |
| 1:100 | 50 μl | 0.046 | 0.244 |

Similar results are obtained using the immobilized anti-HBsAg antibody to capture the antigen and a second soluble anti-HSV1 glycoprotein to detect gD epitopes. In this case color development is proportional to gD epitopes present in the antigen bound to the bead coated with anti-HBsAg antibody. These results are shown in Table 2.

TABLE 2

Glycoprotein D epitopes present in antigen bound to immobilized HBsAg antibody.

| Lysate dilution | μl lysate in assay | Absorbance (492-600 nm units/ml) | |
|---|---|---|---|
| | | control lysate (pHBpreSGAP347/19T) | pDC103 lysate |
| 1:500 | 10 μl | −0.006 | 0.147 |
| 1:100 | 10 μl | 0.136 | 0.458 |
| 1:100 | 50 μl | 0.170 | 1.391 |
| 1:100 | 100 μl | 0.479 | >2.0 |

Results shown in Tables 1 and 2 indicate that both gD and HBsAg epitopes were present in the same molecule. Furthermore, they indicate that the hybrid antigen synthesized in yeast was present assembled into particles, since HBsAg monomers react very poorly with the antibodies in the Abbott Auzyme® immunoassay, which were employed for binding to HBsAg.

2b. Western Analysis

To further confirm that a fusion protein, containing gD and HBsAg epitopes was being synthesized, a Western analysis (previously described) was performed on yeast extracts using sera against gD or a monoclonal antibody against HBsAg.

To this purpose, yeast strain 2150-2-3 was transformed with pDC103, pYHS119, pHBpreSGAP347/19T or pCl/1 (the latter three are controls). Transformants were selected on leu-plates.

Single transformant colonies were inoculated into 2.5 ml of selective leu⁻ medium and were grown for 24 hr at 30° C. An aliquot of 0.5 ml of this saturated culture was inoculated into 50 ml of YEPD containing 0.002% adenine and grown to low density ($A_{650}$ 1.2–2.3). Cells were harvested, and approximately 150 to 300μl of packed cells were resuspended in 100 μl of sample buffer for protein gels (Laemmli, *Nature* (1970) 227:680). Samples were boiled, vortexed and insoluble material was removed by centrifugation.

An aliquot (25 μl) of each sample was loaded onto each of two 10% polyacrylamide gels (Laemmli, supra). Both gels were electrophoresed at the same time. After electrophoresis, proteins were blotted onto nitrocellulose filters (BA 85, 0.45 μm, Schleicher and Schuell) following the procedure of Towbin et al. (*Proc. Natl. Acad. Sci. U.S.A.* (1979) 76:4350).

One filter was treated with rabbit anti-HSV1 glycoprotein antibody and color was developed using a second goat anti-rabbit antibody conjugated with horseradish peroxidase (as previously described). Using this procedure, a strong band of approximately 65 kd was detected in extracts of yeast cells transformed with pDC103. This molecular weight is very close to the expected size (64.6 kd) of the preS-HBsAg-gD fusion, calculated from the cloned DNA sequence. Therefore, the results indicated that a fusion protein was being synthesized in yeast transformed with pDC103. As expected, a much smaller band (~30 kd) which has the expected size for gD was detected in extracts of yeast cells transformed with pYHS119, while no bands reactive with anti-gD were detected in extracts from pCl/1 or pHBpreSGAP347/19T transformants.

The second identical filter was treated with a monoclonal antibody (3A11) against HBsAg and color was developed using a second goat anti-mouse antibody conjugated with horseradish peroxidase (previously described). Using this procedure a 65 kd band was detected in extracts of yeast cells transformed with pDC103, while a 30 kd band was detected in extracts from cells transformed with pHBpreSGAP347/19T and no bands were present in extracts of pYHS119 or pCl/l transformants. These results confirmed that a fusion protein which contains both gD and HBsAg epitopes, was being synthesized in yeast cells carrying pDC103. This fusion protein had the expected size (65 kd) to account for the gD (30 kd) and HBsAg (30 kd) fragments.

3. The gD-HBsAg Fusion Protein Is Assembled Into Particles

To confirm that the preS-HBsAg-gD fusion protein was being assembled into particles, lysates of strains transformed with pDC103 were submitted to density gradients in CsCl. Lysates from cells harboring pHBpreSGAP347/19T were used as control.

Single transformant colonies were inoculated into 2.5 ml of selective leu⁻ medium and were grown for 30 hr at 30° C. An aliquot of 2 ml of this saturated culture was used to inoculate 200 ml of selective leu⁻ medium and cells were grown at 30° C. until an $OD_{650}$ 1 to 3. Cell free lysates were prepared by agitation with glass beads in lysis buffer (10 mM $NaPO_4$, pH 7.5, 0.1% Triton X-100) and removal of cell debris by centrifugation. An aliquot of 0.6 ml was loaded onto a CsCl gradient prepared by adding 5.3 ml of a solution of 1.4 gm CsCl per ml of 10 mM $NaPO_4$, pH 7.5 and overlaying it with 5.3 ml of a solution of 1.4 gm CsCl per ml of the same buffer in a SW-41 polyallomer tube.

Gradients were centrifuged at 30 Krpm for 36 hr at 4° C. Twenty-three 0.5 ml fractions were collected and HBsAg activity was detected in each of them using the Abbott Auzyme® assay. Protein was determined by the Bio-Rad assay. Table 3 shows the results obtained. Lysates from cells harboring the hybrid construction (pDC103) contain a single peak of HBsAg activity banding in fractions 8 to 12 with maximal activity in fraction 10, corresponding to about 1.25 gm CsCl/ml. This activity comigrates with that detected in control lysates indicating that the preS-HBsAg-gD fusion protein is being assembled into particles similar to those obtained with HBsAg alone, which appears to be enveloped.

TABLE 3

HBsAg activity in fractions of CsCl gradient.

| Fraction Number | HBsAg Activity* (ng/ml) pDC103 lysate† | control lysate (pHBpreSGAP347/19T)†† |
|---|---|---|
| 1 | 0 | 310 |
| 2 | 4 | 400 |
| 3 | 12 | 500 |
| 4 | 10 | 640 |
| 5 | 10 | 760 |
| 6 | 22 | 1,300 |
| 7 | 138 | 2,300 |
| 8 | 330 | 5,200 |
| 9 | 2,800 | 19,800 |
| 10 | 3,800 | 75,000 |
| 11 | 1,240 | 44,000 |
| 12 | 430 | 6,800 |
| 13 | 106 | 1,700 |
| 14 | 40 | 1,300 |
| 15 | 38 | 330 |
| 16 | 4 | 210 |
| 17 | 4 | 48 |
| 18 | 16 | 72 |
| 19 | 12 | 155 |
| 20 | 30 | 370 |
| 21 | 8 | 30 |
| 22 | 28 | 15 |
| 23 | 150 | 155 |

*HBsAg activity determined by the Abbott Auzyme ® assay.
†HBsAg activity of lysate loaded on gradient; 6.5 μg/ml.
††HBsAg activity of lysate loaded on gradient; 34 μg/ml.

4. Construction of pCl/l-MCS Expression Vectors For the Hybrid Antigen (preS-HBsAg-CS)

4.a. Synthesis of the MCS coding region and cloning into pDC101

The plasmid pCl/l-MCS is a hybrid of a repeat region from *Plasmodium falciparum* circumsporozoite (CS) in conjunction with HBSAg-PreS. The genes encoding the CS proteins of *P. falciparum* have been cloned and the structures of the polypeptides elucidated (Dame et al., *Science* (1984)-225:593 and Enea et al., *Science* (1984) 225:628, both of which are incorporated herein by reference). The primary immunodominant epitopes are located within a large domain of the CS molecule formed by tandem repeated sequences.

Oligomers encoding the four amino acide repeat Asn.Ala.Asn.Pro, which comprises 37 out of 41 repeat tetrads of the *P. falciparum* CS, were kinased and ligated to form concatemers of varying lengths. Kinased linkers, encoding Asn.Val.Asp.Pro (4/41 tetrads), were ligated to both ends creating EcoRI overhangs and several other restriction sites for screening orientation. The sequence of both the repeat tebrads and endlinkers is shown below.

*P. Falciparum* CS

```
                        (Core - 36 mer duplex)n
        AsnAlaAsnProAsnAlaAsnProAsnAlaAsnPro
        AATGCCAACCCAAACGCTAATCCTAACGCAAACCCT
              TTGGGTTTGCGATTAGGATTGCGTTTGGGAATTACGGn
Linkers 1 and 2                      Linkers 3 and 4
                                            SalI  SmaI
AsnSerAsnValAspPro          AsnAlaAsnProAsnValProGly    EcoRI
AATTCCAATGTAGATCCA          AATGCCAATCCTAACGTCGACCCCGGG
    GGTTACATCTAGGTTTACGG          TTAGGATTGCAGCTGGGGCCCTTAA
EcoRI
```

This ligation mixture was digested with EcoRI and run on a 5% native acrylamide gel. A band spanning 300–600 base pairs was cut out, eluted and ligated into pDC101 (described previously) which had been linearized with EcoRI and phosphatased as described in Section 1a. Seven inserts ranging in size from 1–10 repeats were isolated (see Table 4).

In order to isolate the BamHI expression cassette containing the CS repeats for cloning into pCl/l (previously described), the repeats were initially cloned into pHG101. This vector is identical to pDC101, but lacks a BamHI site in the preS coding region.

For the construction of pHG101 the following procedure was followed: pDC101 was completely digested with EcoRI, then partially digested with BamHI. The largest fragment resulting from the digestion was purified by cutting the corresponding band out of a 1% agarose gel and eluting the DNA. This fragment was subsequently phosphated. The procedure removed 30 base pairs of preS coding region between the EcoRI site and the BamHI site. The deleted sequence was replaced by ligating, to the fragment, kinased 30-mers that code for the same amino acids present in pDC101, but which do not regenerate the BamHI site (sequence is shown below).

|  |  |
|---|---|
|  | AsnSerThrAlaPheHisGlnThrLeuGlnAsp |
| 5' | AATTCCACTGCCTTCCACCAAACTCTGCAA |
| 3' | GGTGACGGAAGGTGGTTTGAGACGTTCTAG |
| EcoRI | ΔBamHI |

EcoRI fragments from four PDC101 clones (indicated in Table 4) were subcloned into pHG101. For this purpose, the pDC101-MCS plasmids were digested with EcoRI. The inserts were purified by gel electrophoresis and ligated to pHG101, which had been previously digested with EcoRI and treated with alkaline phosphatase. The resulting plasmids (PHG101-MCS, see Table 4) were used in the preparation of yeast expression vectors.

TABLE 4

Circumsporozoite-HBsAg Clones

| Insert number | Number of Repeats | pDC101 derivative | pHG101 derivative |
|---|---|---|---|
| MCS 29* | 1 | pDC101-MCS29 | pHG101-MCS29 |
| MCS 36* | 3 | pDC101-MCS36 |  |
| MCS 33* | 4 | pDC101-MCS33 | pHG101-MCS33 |
| MCS 31* | 6 | pDC101-MCS31 | pHG101-MCS31 |
| MCS 12* | 10 | pDC101-MCS12 | pHG101-MCS12 |
| MCS 28* | 7 | pDC101-MCS28 |  |
| MCS 34* | 1 | pDC101-MCS34 |  |

*Inserts have been sequenced by M13 dideoxy method (described infra).

4b. Construction of pCl/1-MCS by cloning the BamHI expression cassette from HG101-MCS into pCl/l Plasmids pHG101-MCS29, pHG101-MCS33 and PHG101-MCS31 were digested with BamHI. The resulting fragment containing the hybrid antigen under the control of the GAPDH promoter and terminator, was purified by gel electrophoresis and ligated to BamHI digested, alkaline phosphatase treated pCl/l (described previously). Ligation was carried out for 3 hr at room temperature. The reaction mixture was precipitated with ethanol, resuspended in water and used to transform *E. coli* HB101. Plasmids pCl/l-MCS29, pCl/l-MCS33 and pCl/l-MCS31, were thus obtained..

5. Demonstration That Malaria Circumsporozite Epitopes and HBsAg Epitopes Are Present in a Fusion Protein To confirm that a fusion protein containing MCS and HBsAg epitopes were being synthesized, a Western analysis (previously described) was performed on yeast extracts using monoclonal antibodies against MCS or HBsAg.

To this purpose, yeast strain *Saccharomyces cerevisiae* PO17 (mat a, leu 2-04, cir°) was transformed with pCl/l-MCS29 (or pCl/1-MCS31 or pCl/1-MCS33), pHBpreSGA347/19T or pCl/l (the latter two are controls). Transformants were selected on leu-plates.

Single transformant colonies were inoculated into 2.5 ml of selective leu⁻ medium and were grown for 24 hr at 30° C. An aliquot of 0.5 ml of this saturated culture was inoculated into 50 ml of YEPD and grown to low density ($A_{650}$ 1.2–2.3). Cells were harvested, and approximately 150 to 300μl of packed cells were resuspended in 100 μl of sample buffer for protein gels (Laemmli, *Nature* (1970) 227 680). Samples were boiled, vortexed and insoluble material was removed by centrifugation.

An aliquot (25 μl) of each sample was loaded onto each of two 10% polyacrylamide gels (Laemmli, supra). Both gels were electrophoresed at the same time. After electrophoresis, proteins were blotted onto nitrocellulose filters (BA 85, 0.45 μm, Schleicher and Schuell) following the procedure of Towbin, et al. (*Proc. Natl. Acad. Sci. U.S.A.* (1979) 76:4350). One filter was treated with monoclonal anti-MCS antibody (2A-10) and color was developed using a second goat anti-mouse antibody conjugated with horse-radish peroxidase (as previously described).

As expected, no bands reactive with anti-MCS were detected in extracts from pDC103 transformants. Bands of about 30 kd, 34 kd, and 35 kd were detected in extracts from yeast transformed with pCl/l-MCS29 (one repeat), pCl/l-MCS33 (four repeats) and pCl/l-MCS31 (six repeats). All bands reacted with monoclonal antibody (3A11) against HBsAg when a second identical filter was submitted to Western analysis.

These results show that a fusion protein containing both MCS and HBsAg epitopes was being synthesized in yeast cells harboring pCl/l-MCS plasmids. The fusion protein had the expected size to account for both MCS and HBsAg fragments.

To further confirm that the hybrid antigen in yeast was present and assembled into particles, an ELISA assay for HBsAg was performed with the extracts of transformants. Since the HBsAg monomers react very poorly with the antibodies in the Abbott-Auzyme® immuno-assay, reactivity of the extracts in the ELISA is indicative of the presence of assembled particles.

ELISA results from extracts of yeast transformed with pCl/l-MCS29 indicated an expression level of particles of about 0.63–2.06 mg/l, while for pCl/l-MCS33, this value was about 0.22–1.22 mg/l.

The above results demonstrate that by employing hybrid DNA constructions expressing a particle forming polypeptide fused to a polypeptide having an epitope of interest, particles can be produced in cells, particularly unicellular microorganisms, where epitopic sites of both the particle forming protein and the epitope of interest are presented. In this manner, immunogens are produced which allow for the production of antibodies, to both the epitopes of the particle forming polypeptide and the epitope(s) of the native polypeptide of interest fused to the particle forming polypeptide, which polypeptide of interest is not naturally joined to the particle forming polypeptide. In this manner, epitopes of low antigenicity can result in the formation of antibodies having high binding specificity and/or high titer. In addition, safe, effective vaccines can be provided where an effective immune response can be obtained. Furthermore, by employing a plurality of hybrid genes, particles can be obtained, having epitopes of different pathogens, so that the same particle may serve as a carrier for vaccination against different strains of the same species, diverse pathogens, or the like.

Although the foregoing invention has been described in some detail by way of illustration and example for purposes of clarity of understanding, it will be obvious that certain changes and modifications may be practiced within .the scope of the appended claims.

What is claimed is:

1. A method for inducing an immune response to one or more epitopes of interest which comprises:

immunizing a host with a particle comprising at least in part a hybrid polypeptide comprising a particle forming polypeptide fused to one or more polypeptides of interest, where said polypeptide of interest defines an epitopic site of a pathogen or toxin and is disposed within said particle such that said epitopic site is immunologically reactive.

2. A method according to claim 1, wherein said particle forming polypeptide is at least a portion of the Hepatitis B surface antigen.

3. A method according to claim 2, wherein said polypeptide of interest is fused to said particle forming polypeptides through at least a portion of the pre-surface polypeptide.

4. A method according to claim 1, wherein said particle forming polypeptide is the Hepatitis B surface antigen.

5. A method according to claim 4, wherein said polypeptide of interest is fused to said particle forming polypeptide through at least a portion of the pre-surface polypeptide of the Hepatitis B surface antigen.

* * * * *